(12) United States Patent
Fukuda et al.

(10) Patent No.: US 8,075,489 B2
(45) Date of Patent: Dec. 13, 2011

(54) ULTRASOUND DIAGNOSTIC APPARATUS

(75) Inventors: Osamu Fukuda, Saga (JP); Naohiro Ueno, Saga (JP); Masayoshi Tsubai, Saga (JP); Morito Akiyama, Saga (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 709 days.

(21) Appl. No.: 12/161,921

(22) PCT Filed: Jan. 23, 2007

(86) PCT No.: PCT/JP2007/050983
§ 371 (c)(1),
(2), (4) Date: Jul. 23, 2008

(87) PCT Pub. No.: WO2007/086373
PCT Pub. Date: Aug. 2, 2007

(65) Prior Publication Data
US 2009/0036779 A1 Feb. 5, 2009

(30) Foreign Application Priority Data

Jan. 24, 2006 (JP) .................................. 2006-015518
Jan. 18, 2007 (JP) .................................. 2007-008790

(51) Int. Cl.
*A61B 8/14* (2006.01)
*A61B 5/103* (2006.01)
(52) U.S. Cl. ........................................ 600/459; 600/587
(58) Field of Classification Search .................. 600/459, 600/587
See application file for complete search history.

(56) References Cited

U.S. PATENT DOCUMENTS 5,520,785 A * 5/1996 Evans et al. ............. 204/192.27
5,833,634 A 11/1998 Laird et al.

FOREIGN PATENT DOCUMENTS

| JP | 2005-066041 A | 3/2005 |
| JP | 2005-270341 A | 10/2005 |
| JP | 2005-321369 A | 11/2005 |
| WO | 97-17017 A1 | 5/1997 |
| WO | 2006-40967 A1 | 4/2006 |

OTHER PUBLICATIONS

International Search Report of PCT/JP2007/050983, date of mailing Apr. 10, 2007.

* cited by examiner

*Primary Examiner* — Michael Rozanski
(74) *Attorney, Agent, or Firm* — Westerman, Hattori, Daniels & Adrian, LLP

(57) ABSTRACT

Pressure distribution on a surface of an ultrasonic probe can be measured directly. Piezoelectric sensors, in which a piezoelectric thin film is formed on a film-like substrate, are arranged in the form of an array on the surface of an ultrasonic probe, and a sensor output signal processing unit outputs pressure measured for each piezoelectric sensor S1, S2 to S9 based on output signals from each of the piezoelectric sensors to an image processing unit. The image processing unit generates a histogram of the measured pressures for piezoelectric sensors S1, S2 to S9, and displays the histogram, while plotting the piezoelectric sensors on the X axis and the measured pressures on the Y axis, along with the resulting ultrasound tomographic image, on a monitor.

9 Claims, 15 Drawing Sheets

FIG.14
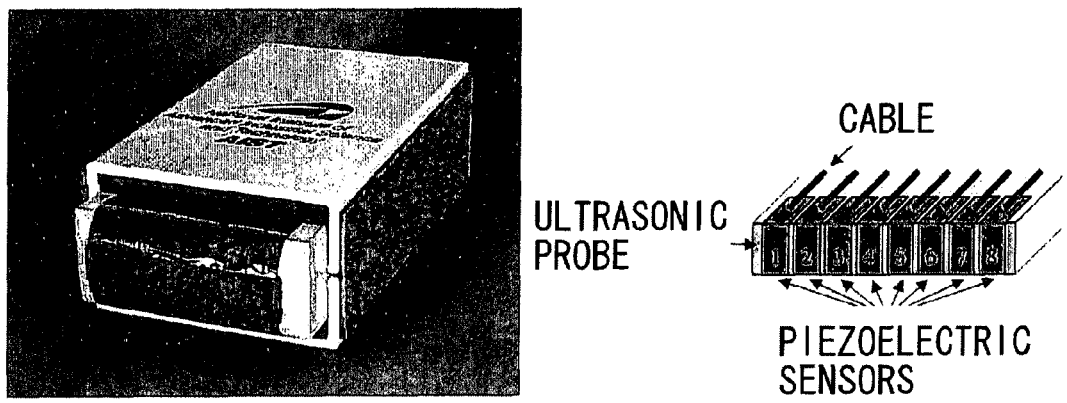
FIG.15
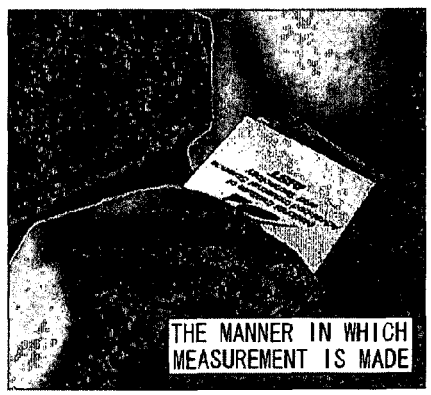
FIG.16(a)    FIG.16(b)
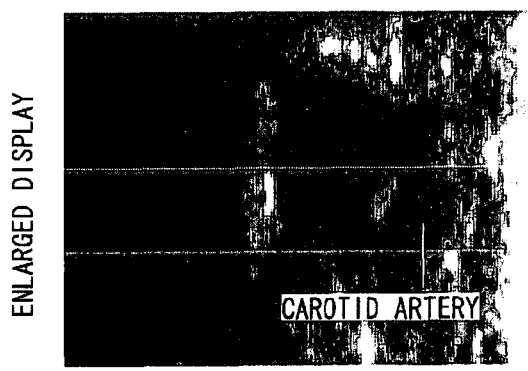
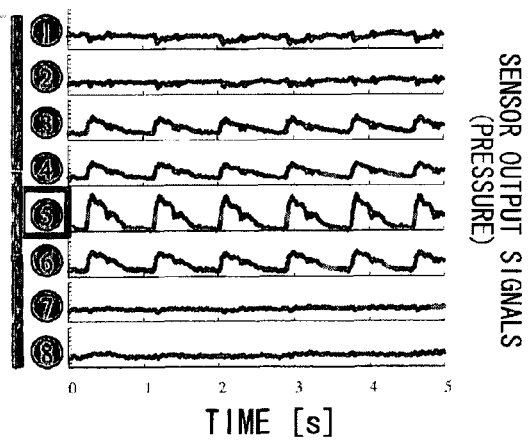

FIG.17(a)   FIG.17(b)   FIG.17(c)
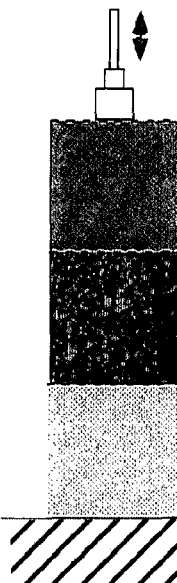
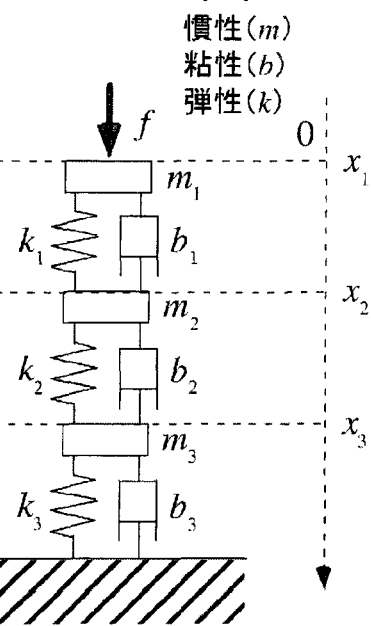
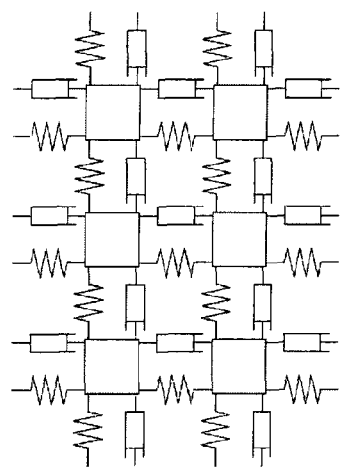
FIG.18
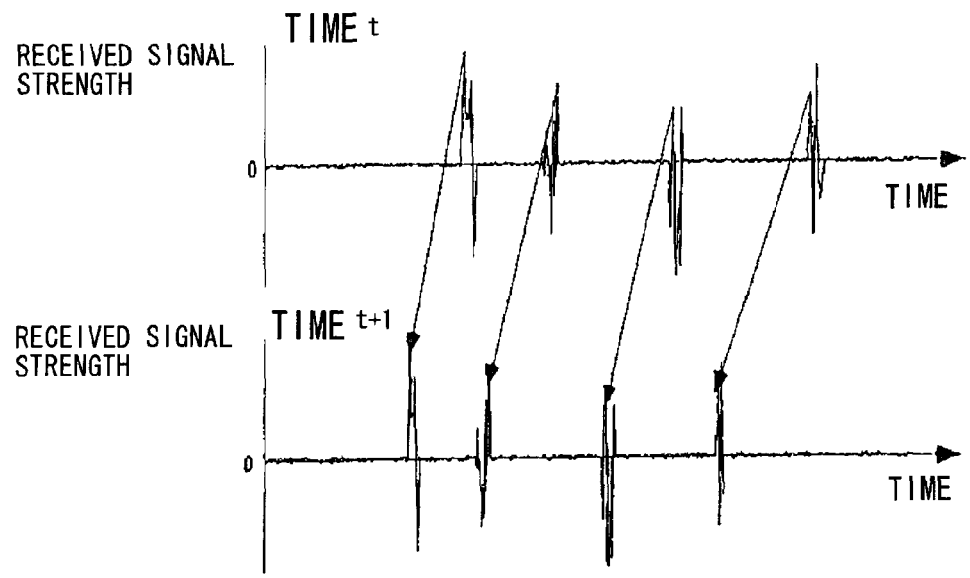

hard  medium  soft

ULTRASONIC PROBE

|  | ELASTICITY (N/m) | VISCOSITY (N/m$^2$) | INERTIA (Kg) |
|---|---|---|---|
| TISSUE LAYER 1 | 1081.5 | 0 | 0 |
| TISSUE LAYER 2 | 1352.9 | 0 | 0 |
| TISSUE LAYER 3 | 12323.3 | 39.3 | 2.1 |

ULTRASOUND DIAGNOSTIC APPARATUS

TECHNICAL FIELD

The present invention relates to an ultrasound diagnostic apparatus which is provided with an ultrasonic probe that contacts a specimen, and which generates an ultrasound tomographic image by transmission and reception of ultrasonic waves through the ultrasonic probe, and more particularly, to an ultrasound diagnostic apparatus that measures pressure distribution on the surface of an ultrasonic probe.

BACKGROUND

Numerous ultrasound diagnostic apparatuses have been developed in the past that generate ultrasound tomographic images of the interior of a specimen by utilizing ultrasonic waves output from an ultrasonic probe. In addition, such ultrasound diagnostic apparatuses employ technologies for acquiring pressure data generated on the surface of the interior of a specimen. For example, according to the technology described in Patent Document 1, pressure applied to a specimen is calculated from the movement distance of an ultrasonic probe and the contact surface area of the specimen. In addition, according to the technology described in Patent Document 2, the modulus of elasticity of an area of the interior of a specimen is calculated from variations in that area and separately measured blood pressure.

[Patent Document 1] Japanese Patent Application Laid-open No. 2004-089362

[Patent Document 2] Japanese Patent Application Laid-open No. 2001-292995

The technology described in Patent Document 1 does not involve direct measurement of pressure applied to an ultrasonic probe, but rather calculates pressure from other indicators. In addition, the technology described in Patent Document 2 measured blood pressure with a blood pressure measuring unit separately and independently from an ultrasonic probe. Namely, the prior art does not involve direct measurement of pressure on the surface of an ultrasonic probe, but rather that pressure is obtained by an indirect method, thereby resulting in problems with reliability.

DISCLOSURE OF THE INVENTION

With the foregoing in view, a first object of the present invention is to provide an ultrasound diagnostic apparatus capable of directly measuring pressure on the surface of an ultrasonic probe.

In addition, pressure distribution on the surface of the ultrasonic probe is not uniform depending on the specimen. For example, in the case the specimen is a human body, since the surface of the body has numerous curves and surface irregularities, and since there are also variations in surface hardness due to the presence of bone, tendon, muscle, blood vessels and the like, there are virtually no instances in which pressure acting on the surface of the probe is uniform. Moreover, pressure acting on the surface of the ultrasonic probe is also affected by the manner in which the ultrasonic probe is pressed against a specimen. Namely, various pressures from a specimen act on each region of the surface of an ultrasonic probe, and information regarding the distribution of those pressures serves as an effective indicator of the manner in which pressure is acting during acquisition of generated ultrasound tomographic images.

With the foregoing in view, a second object of the present invention is to provide an ultrasound diagnostic apparatus capable of measuring pressure distribution on the surface of an ultrasonic probe.

The present invention provides the following means for solving the above-mentioned problems. Furthermore, although reference symbols used in the explanation of the best mode for carrying out the present invention and the drawings to be subsequently explained are indicated in parentheses for reference purposes, the constituent features of the present invention are not limited to those indicated with the reference symbols.

An ultrasound diagnostic apparatus of the present invention as claimed in claim 1 is an ultrasound diagnostic apparatus (1) which is provided with an ultrasonic probe (10) that contacts a specimen, and which generates an ultrasound tomographic image by transmitting and receiving ultrasonic waves through the ultrasonic probe, wherein a plurality of sheet-like piezoelectric sensors (100) are arranged on or in the vicinity of a surface (10*a*) of the ultrasonic probe, measuring means (sensor output signal processing unit 40) is provided for measuring pressure distribution on the surface, based on the arrangement of each of the plurality of piezoelectric sensors on the surface and output signals from the piezoelectric sensors, and display means (image processing unit 50, monitor 60) is provided for displaying the pressure distribution in a visible form.

An ultrasound diagnostic apparatus of the present invention as claimed in claim 2 is the ultrasound diagnostic apparatus (1) of claim 1, wherein the piezoelectric sensors (100) comprise a piezoelectric aluminum nitride thin film formed on a film-like substrate.

An ultrasound diagnostic apparatus of the present invention as claimed in claim 3 is the ultrasound diagnostic apparatus (1) of claim 1, wherein the piezoelectric sensors (100) are arranged in the form of an array or a matrix on or in the vicinity of the surface (10*a*).

An ultrasound diagnostic apparatus of the present invention as claimed in claim 4 is the ultrasound diagnostic apparatus (1) of any one of claims 1 to 3, wherein the display means (image processing unit 50, monitor 60) displays so as to enable comparison between the pressure distribution and the ultrasound tomographic image.

An ultrasound diagnostic apparatus of the present invention as claimed in claim 5 is the ultrasound diagnostic apparatus (1) of claim 4, wherein the display means (image processing unit 50, monitor 60) displays an image composed in the form of an aggregate of image regions corresponding to the arrangement of each piezoelectric sensor (100), an output signal from each piezoelectric sensor being reflected in an image value of the image region corresponding to that sensor.

An ultrasound diagnostic apparatus of the present invention as claimed in claim 6 is the ultrasound diagnostic apparatus (1) of claim 1, wherein the measuring means (sensor output signal processing unit 40) accumulates an output signal at each time for each piezoelectric sensor (100) for a prescribed amount of time, and measures a fluctuation status (signal velocity, signal period) in the specimen or specifies the location of a fluctuation site based on time-based changes in the accumulated output signals and the arrangement on the surface (10*a*) of the piezoelectric sensors.

An ultrasound diagnostic apparatus of the present invention as claimed in claim 7 is the ultrasound diagnostic apparatus (1) of claim 6, wherein the display means (image processing unit 50, monitor 60) displays to enable comparison between the accumulated output signals and the ultrasound tomographic image, and displays an output signal of each piezoelectric sensor (100) while arranging in parallel image regions corresponding to the arrangement of the piezoelectric sensors (100) in the ultrasound tomographic image.

An ultrasound diagnostic apparatus of the present invention as claimed in claim 8 is the ultrasound diagnostic apparatus (1) of claim 6, wherein the measuring means (sensor output signal processing unit 40) measures the velocity of prescribed signals (triangle waves) between a plurality of piezoelectric sensors based on the arrangement interval of the piezoelectric sensors (100) and the output time difference of those prescribed signals.

An ultrasound diagnostic apparatus of the present invention as claimed in claim 9 is the ultrasound diagnostic apparatus (1) of claim 6, wherein the measuring means (sensor output signal processing unit 40) measures the period of a prescribed signal (triangle wave) based on the output interval of that prescribed signal in a specific piezoelectric sensor (100).

An ultrasound diagnostic apparatus of the present invention as claimed in claim 10 is the ultrasound diagnostic apparatus (1) of claim 6, wherein the measuring means (sensor output signal processing unit 40) specifies the piezoelectric sensor (100) that initially outputs a prescribed signal (triangle wave), and the display means (image processing unit 50, monitor 60) displays the arrangement (channel number) of that piezoelectric sensor.

An ultrasound diagnostic apparatus of the present invention as claimed in claim 11 is the ultrasound diagnostic apparatus (1) of claim 6, wherein the measuring means (sensor output signal processing unit 40) specifies the piezoelectric sensor (100) that outputs a signal for which the peak-to-peak amplitude (mean value of 10 measurements of peak-to-peak amplitude for 1 second) reaches a maximum, and the display means (image processing unit 50, monitor 60) displays the arrangement (channel number) of that piezoelectric sensor.

An ultrasound diagnostic apparatus of the present invention as claimed in claim 12 is the ultrasound diagnostic apparatus (1) of either of claims 10 or 11, wherein the display means (image processing unit 50, monitor 60) displays the ultrasound tomographic image in a form that allows specification of an image region corresponding to the arrangement of the specified piezoelectric sensor (100).

An ultrasound diagnostic apparatus of the present invention as claimed in claim 13 is the ultrasound diagnostic apparatus (1) of claim 12, wherein the display means (image processing unit 50, monitor 60) displays an enlarged view of the corresponding image region.

An ultrasound diagnostic apparatus of the present invention as claimed in claim 14 is the ultrasound diagnostic apparatus (1) of claim 1, provided with deformation amount measuring means (image processing unit 50) for measuring the amount of deformation of each tissue layer constituting the specimen, based on ultrasonic wave information (ultrasonic signal) obtained by the transmission and reception of ultrasonic waves, and estimation means (image processing unit 50) for estimating the value of elasticity, viscosity or inertia of each of the tissue layers from a signal output of the piezoelectric sensors (100) and the measured deformation amount of the specimen based on the elasticity, viscosity and inertia of the specimen along with an equation of motion of a physical model describing the relationship between force applied to the specimen and the amount of deformation of each layer constituting the specimen.

According to the ultrasound diagnostic apparatus as claimed in claim 1, pressure distribution on the surface of an ultrasonic probe can be measured directly, thereby allowing the obtaining of highly reliable values. In addition, the use of sheet-like piezoelectric sensors enables the piezoelectric sensors to be composed with adequate thinness to a degree that does not have an effect on ultrasonic wave measurement.

According to the ultrasound diagnostic apparatus as claimed in claim 2, since the piezoelectric sensors can be made to have superior heat resistance, the piezoelectric sensors have sensitivity characteristics with extremely low temperature dependency, thereby eliminating the need for superfluous correction circuits.

According to the ultrasound diagnostic apparatus as claimed in claim 3, pressure distribution of the surface of an ultrasonic probe can be measured in detail.

According to the ultrasound diagnostic apparatus as claimed in claim 4, conditions as to what type of pressure is acting during acquisition of the ultrasound tomographic image can be ascertained.

According to the ultrasound diagnostic apparatus as claimed in claim 5, detailed pressure distribution on the surface of an ultrasonic probe can be determined at a glance.

According to the ultrasound diagnostic apparatus as claimed in claim 6, fluctuations within a specimen or a location of a fluctuation site can be acquired.

According to the ultrasound diagnostic apparatus as claimed in claim 7, the extraordinary effect is obtained in which what type of pressure fluctuation has occurred in each image region can be understood.

According to the ultrasound diagnostic apparatus as claimed in claim 8, the status of a generation source of a signal can be estimated from the velocity of the signal.

According to the ultrasound diagnostic apparatus as claimed in claim 9, the status of a generation source of a signal can be estimated from the period of the signal.

According to the ultrasound diagnostic apparatus as claimed in claim 10, a location of a fluctuation site within a specimen can be estimated.

According to the ultrasound diagnostic apparatus as claimed in claim 11, a location of a fluctuation site within a specimen can be estimated without being affected by the manner in which the ultrasonic probe is pressed against the specimen or local pressure changes within the contact surface.

According to the ultrasound diagnostic apparatus as claimed in claim 12, a location of a fluctuation site within an ultrasound tomographic image can be estimated easily.

According to the ultrasound diagnostic apparatus as claimed in claim 13, the extraordinary effect is obtained in which a location of a fluctuation site within an ultrasound tomographic image can be estimated.

According to the ultrasound diagnostic apparatus as claimed in claim 14, a value of elasticity, viscosity or inertia of each tissue layer composing a specimen can be estimated. In addition, since the use of a plurality of piezoelectric sensors allows the acquisition of pressure distribution within a contact surface, pressure distribution within a contact surface can be estimated in greater detail. Moreover, the use of sheet-like piezoelectric sensors enables highly accurate estimates to be made without being affected by ultrasonic wave information.

BRIEF DESCRIPTION OF THE DRAWINGS

FIG. 2A shows an example of arranging piezoelectric sensors in the form of an array, while

FIG. 4A is a schematic drawing depicting contact by an ultrasonic probe with a specimen while positioned at an angle, while

FIG. 5A is a schematic drawing depicting contact by an ultrasonic probe with a specimen having surface irregularities in the surface thereof, while

FIG. 6A is a schematic drawing depicting contact by an ultrasonic probe with a specimen containing a hard area in the interior thereof, while

FIG. 7A shows a first example of displaying a histogram of pressure distribution and an ultrasound tomographic image on the top and bottom of a monitor, while

FIG. 11A is a drawing showing an overview of an apparatus for measuring damping ratio during transmission and reception of ultrasonic waves, while

FIG. 14 is a drawing showing eight piezoelectric sensors arranged on the surface of an ultrasonic probe in the form of an array;

FIG. 15 depicts the manner in which measurements are made in the vicinity of the carotid artery;

FIG. 16A is an ultrasound tomographic image in the vicinity of the carotid artery, while FIG. 16B shows time series pressure data measured with each piezoelectric sensor;

FIG. 17A is a cross-sectional view showing a specimen having a three-layer structure used during estimation of elasticity, viscosity and inertia of the present invention, FIG. 17B represents a physical model of the specimen composed of elasticity, viscosity and inertia, and FIG. 17C shows a two-dimensional model;

FIG. 18 is a schematic drawing of a signal received by an ultrasonic probe;

FIG. 19A is a photograph of a layered structure composed of three tissue layers, while

1 Ultrasound diagnostic apparatus
10 Ultrasonic probe
40 Sensor output signal processing unit
50 Image processing unit
60 Monitor
100 Piezoelectric sensor

BEST MODE FOR CARRYING OUT THE INVENTION

Figure 1:
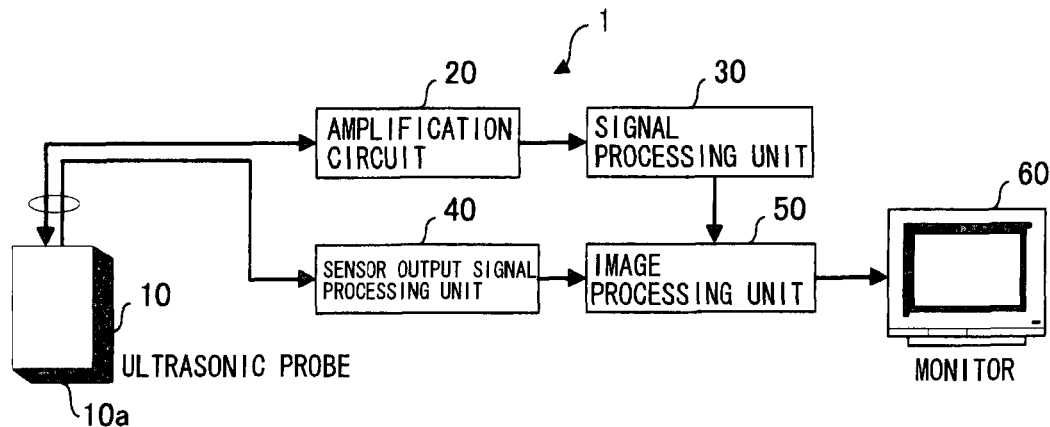
FIG. 1 is a block diagram showing an example of the configuration of an ultrasound diagnostic apparatus of the present invention.

The following provides an explanation of embodiments of the ultrasound diagnostic apparatus of the present invention in accordance with the drawings. FIG. 1 is a block diagram showing an example of the configuration of an ultrasound diagnostic apparatus 1 of the present invention. The basic configuration of the ultrasound diagnostic apparatus 1 consists of an ultrasonic probe 10, an amplification circuit 20, a signal processing unit 30, a sensor output signal processing unit 40, an image processing unit 50 and a monitor 60.

Piezoelectric sensors 100 as shown in FIG. 2 are arranged on a surface 10a of ultrasonic probe 10 that contacts a specimen. In addition, a large number of ultrasonic oscillators are arranged within ultrasonic probe 10, and each ultrasonic oscillator has a function for generating an electrical signal from amplification circuit 20 after converting to ultrasonic waves, and a function for receiving ultrasonic waves reflected from a specimen and outputting to amplification circuit 20 after converting to an electrical signal.

Amplification circuit 20 is connected to the ultrasonic oscillators, and has a function for amplifying high-frequency signals generated with an internal generation circuit to a level that causes the generation of ultrasonic waves by driving the ultrasonic oscillators. In addition, electrical signals output from each ultrasonic oscillator (to be referred to as wave reception signals) are amplified and output to signal processing unit 30.

A number of wave reception signals corresponding to the number of ultrasonic oscillators are respectively and independently incorporated in signal processing unit 30 in the form of wave reception signals. The signal processing unit 30 matches the phase of each wave reception signal and adds a plurality of wave reception signals for which the respective phase thereof has been matched to form reception signals. Reception signals output from the signal processing unit 30 undergo filter processing or other signal processing followed by output to signal processing unit 50. Signal processing unit 50 converts the reception signals to an ultrasound tomographic image that is depicted on monitor 60.

Figure 2A:
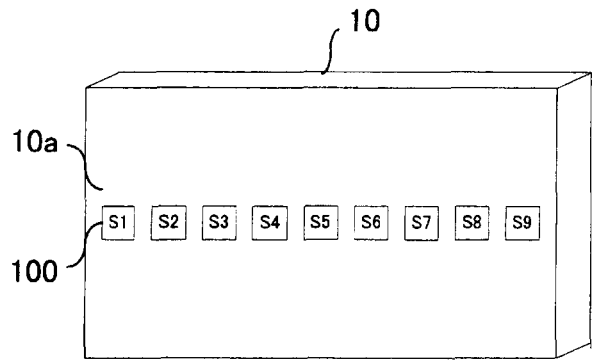
Figure 2B:
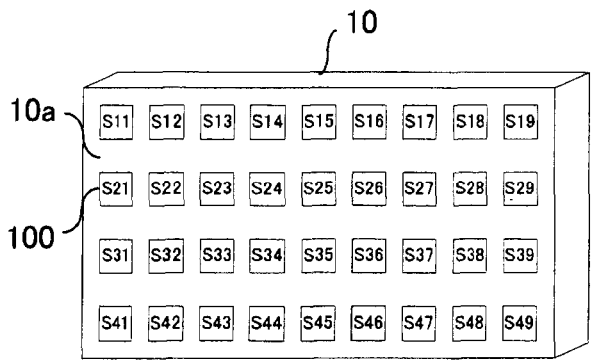
FIG. 2B shows an example of arranging piezoelectric sensors in the form of a matrix.

Piezoelectric sensors 100 are arranged on ultrasonic probe surface 10a in the manner shown in FIG. 2 in this example. In FIG. 2A, an example is shown in which nine piezoelectric sensors 100 in the form of S1 to S9 are arranged in the form of an array. In addition, in FIG. 2B, an example is shown in which 36 piezoelectric sensors 100 in the form of S11 to S19, S21 to S29, S31 to S39 and S41 to S49 are arranged in the form of a matrix. Installing the piezoelectric sensors 100 within a range that allows direct contact with a specimen in this manner is the most preferable in terms of measuring force generated at the boundary between the ultrasonic probe 10 and the specimen.

At this time, piezoelectric sensors 100 preferably have an extremely thin, sheet-like structure to reduce the effects on ultrasonic signals as much as possible, and preferably have high heat resistance to enable disinfection by boiling from the viewpoint of sterilization. Moreover, since there are also cases in which the specimen surface and ultrasonic probe surface 10a may be curved, a flexible material is preferable. A description of the specific structure of these piezoelectric sensors 100 will be subsequently provided.

In the sensor output signal processing unit 40 of FIG. 1, output signals respectively and independently output from each piezoelectric sensor 100 arranged on ultrasonic probe surface 10a are incorporated by an A/D converter, and the pressure thereof is measured from the level of each output signal by a CPU. Moreover, information relating to the arrangement of each piezoelectric sensor 100 on ultrasonic probe surface 10a (for example, order of arrangement or coordinates) and pressure measured for each piezoelectric sensor 100 are correlated and output to image processing unit 50 in the form of pressure distribution information.

In addition, sensor signal processing unit 40 has a temporary storage space, and after having incorporated output signals received from each piezoelectric sensor 100 in the manner previously described, accumulates the output signals for a prescribed amount of time in the form of time series data. The CPU then specifies the piezoelectric sensor 100 to which a prescribed signal, such as a signal of a prescribed level or a signal of waveform having a prescribed characteristic for the phase thereof, has been output at the fastest time, and outputs a channel number that indicates the arrangement of the specified piezoelectric sensor (order of arrangement or coordinates) to the image processing unit 50, after which the image processing unit 50 is able to display the channel number of the specified piezoelectric sensor (for example, S1) or its corresponding location (for example, center of an image) on monitor 60. Namely, a piezoelectric sensor is specified that is the closest to a fluctuation site within a specimen and to which a prescribed signal has been output after having received a pressure from the fluctuation site at the fastest time.

In addition, the sensor output signal processing unit 40 is also able to specify fluctuation status within the specimen from the time series data. For example, the velocity, period and so forth of a prescribed signal can be calculated from the generation interval of that signal and the arrangement of piezoelectric sensors 100, the calculated amount can be output to image processing unit 50 in the form of fluctuation status, and the image processing unit 50 can display the fluctuation status (velocity, period) on monitor 60. Furthermore, discrimination of a prescribed signal in output data from each piezoelectric sensor 100 may be carried out based on the amplification level or based on a characteristic feature of the phase (such as an auto-correlation coefficient).

In addition, sensor output signal processing unit 40 is also able to specify a piezoelectric sensor 100 to which is output the signal having the largest peak-to-peak amplitude among the time series data of each channel. Namely, as shown in the time series data of FIG. 16B, the channel number of the piezoelectric sensor 100 to which is output the signal having the largest amplitude is displayed on monitor 60 by utilizing the property by which pressure fluctuations increase the closer to a fluctuation site and decrease the farther from a fluctuation site within a specimen. More specifically, peak-to-peak amplitude is measured a plurality of times within a prescribed amount of time, and the channel number for which the mean value thereof is the largest is specified. This prescribed amount of time and number of measurements can be set corresponding to the characteristics of the target signal.

In addition to creating ultrasound tomographic images as previously described, image processing unit 50 also processes and displays measured pressure distribution on monitor 60. More specifically, as shown in FIGS. 4 to 7, in the case an array type of arrangement has been specified, or array type arrangement information has been obtained in advance, based on piezoelectric sensor output signals received from the sensor output signal processing unit 40, a histogram is generated in which the order of arrangement of the piezoelectric sensors (S1 to S9) is plotted on the X axis and the pressure F measured by each piezoelectric sensor is plotted on the Y axis, and the histogram is displayed on monitor 60. In addition, as shown in FIG. 8, in the case a matrix type of arrangement has been specified, or matrix type arrangement information has been obtained in advance, based on piezoelectric sensor output signals received from the sensor output signal processing unit 40, a two-dimensional image is generated by making the luminosity of pixel blocks corresponding to the coordinates at which each piezoelectric sensor (S11 to S49) is arranged on ultrasonic probe surface 10a proportional to pressure F measured by that piezoelectric sensor 100, and that image is displayed on monitor 60. A histogram or two-dimensional image created in this manner is displayed with an ultrasound tomographic image by arranging on the top and bottom or on the left and right sides of monitor 60 so as to enable mutual comparison.

Moreover, image processing unit 50 displays ultrasound tomographic images in a form that enables regions corresponding to the arrangement of the applicable piezoelectric sensors 100 in the ultrasound tomographic image to be specified corresponding to piezoelectric sensor 100 output signals received from sensor output signal processing unit 40. For example, as shown in FIG. 16A, among the channel numbers of piezoelectric sensors 100 corresponding to each image region displayed on an ultrasound tomographic image, the channel number of the piezoelectric sensor 100 specified as being closest to a fluctuation site is emphasized by displaying inside a box.

[Piezoelectric Sensors 100]

Figure 10:
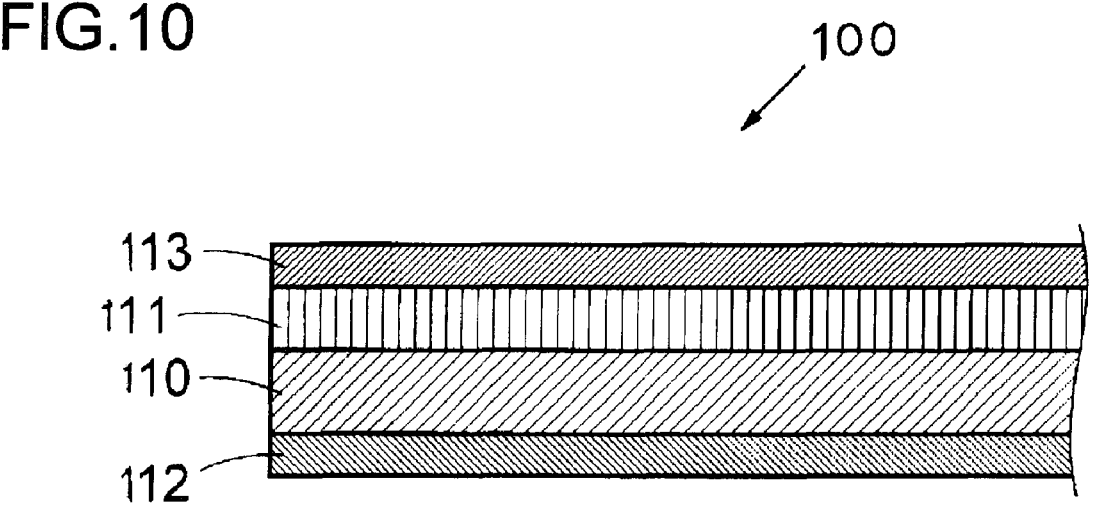
FIG. 10 is a cross-sectional view showing the layer structure of a piezoelectric sensor of the present invention.

The following provides an explanation of the structure of the piezoelectric sensors 100 of the present invention with reference to the drawings. FIG. 10 is a cross-sectional view showing the layer structure of a film-like piezoelectric sensor 100 used in the ultrasound diagnostic apparatus of the present invention. This piezoelectric sensor 100 employs the basic structure of a sensor for use in an ultrasound diagnostic apparatus.

A substrate 110 is a flexible film composed of a polymer material, and a piezoelectric layer 111 is formed on the upper side of this substrate 110. A polyimide film, for example, can be used for the substrate 110. The piezoelectric layer 111 is an aluminum nitride (AlN) thin film. Aluminum nitride piezoelectric materials exhibit c-axis orientation on polyimide film, and have been confirmed to demonstrate adequate piezoelectricity. In addition, polyimide film is also superior in terms of heat resistance.

Furthermore, although piezoelectric layer 111 is preferably an aluminum nitride thin film, other metal compounds having piezoelectricity can also be used. Examples of piezoelectric metal compounds that can be used in addition to aluminum nitride include zinc oxide, gallium nitride, indium nitride and lithium niobate. Namely, although metal compounds such as aluminum nitride, zinc oxide, gallium nitride, indium nitride and lithium niobate can be used for piezoelectric layer 111, in consideration of such factors as heat resistance and temperature characteristics of sensor output, aluminum nitride and zinc oxide are preferable, while aluminum nitride is most preferable.

Although piezoelectric layer 111 can be formed by sputtering, other thin film formation methods may also be used, such as ion plating or CVD. In the case of forming a thin film of piezoelectric layer 111 using sputtering in particular, the degree of crystal orientation of piezoelectric layer 111 can be enhanced, which is preferable since this enables improvement of piezoelectric characteristics. High-frequency magnetron sputtering, for example, can be used for the sputtering method. Although the thickness of piezoelectric layer 111 is preferably 0.5 to 10 µm, if it is excessively thin, film thickness may become uneven, while if excessively thick, an excessive amount of time is required for film deposition. Thus, a thickness of about 1 µm is preferable.

In the case of using aluminum nitride deposited using sputtering for piezoelectric layer 111, the aluminum nitride does not lose piezoelectricity even in high-temperature environments of 600° C. or higher due to the absence of a Curie point, thus resulting in a piezoelectric sensor having superior heat resistance. In addition, since the temperature dependency of sensitivity characteristics is extremely small, there is no need for superfluous correction circuits. In addition to polyimide (PI), polymer films made of, for example, polyethylene naphthalate (PEN) or polyethylene terephthalate (PET) can also be used for substrate on which the thin film piezoelectric material is laminated.

Substrate 110 preferably has adequate flexibility and mechanical strength as well as heat resistance of 100° C. or higher, and polyimide is the most preferable due to its superior mechanical strength and heat resistance. If substrate 110 is excessively thin, mechanical strength becomes inadequate, while if excessively thick, electrical loss increases. Thus, a thickness within the range of 1 to 10 µm is preferable.

Moreover, a first electrode layer 112 and a second electrode layer 113 are formed in the lower side of substrate 110 and the upper side of piezoelectric layer 111, respectively. A platinum (Pt) thin film having a thickness of about 0.1 µm (100 nm) can be used for first electrode layer 112 and second electrode layer 113. Various types of metals, such as platinum, gold, silver or copper, as well as electrically conductive substances, can be used for these electrode layers. It is preferable that platinum is used to inhibit the corrosion of electrode layers. The electrode layers can be formed by commonly used methods such as sputtering, vapor deposition or screen printing. The electrode layers are preferably formed by sputtering to enhance adhesion with substrate 110 and piezoelectric layer 111.

[Damping Characteristics of Piezoelectric Sensors 100]

Figure 11A:
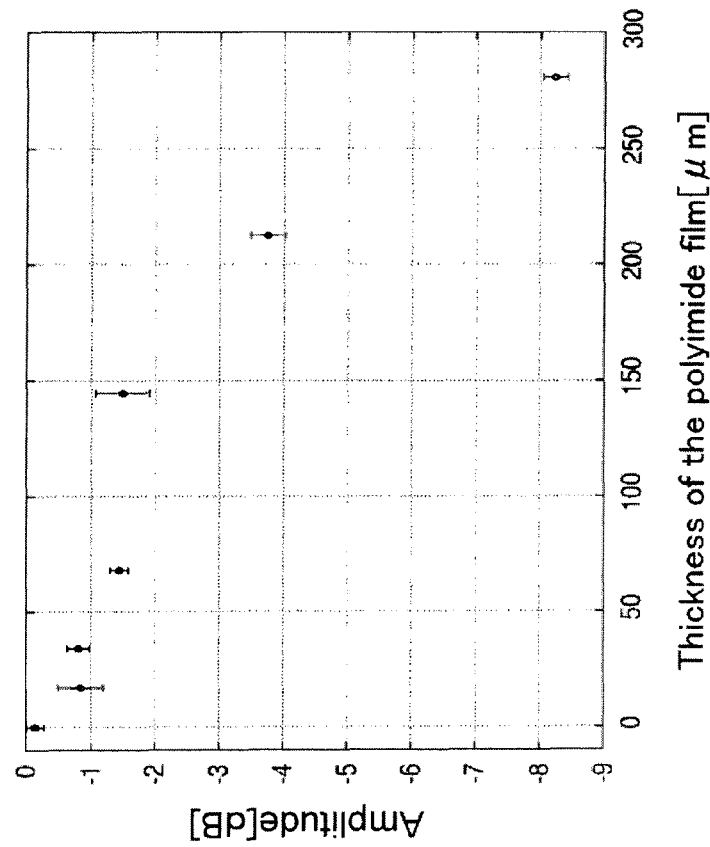
Figure 11B:
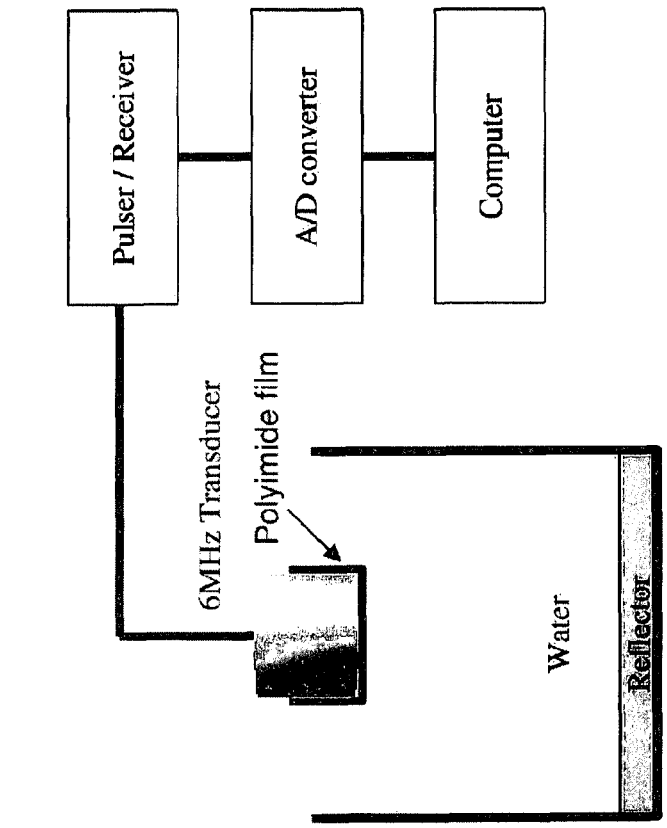
FIG. 11B shows the results of measurements obtained from the apparatus.

FIG. 11A is a drawing showing an overview of an apparatus for measuring damping ratio during transmission and reception of ultrasonic waves, while FIG. 11B shows the results of measurements obtained from the apparatus, indicating the damping ratio of ultrasonic waves versus the thickness of polyimide film composing piezoelectric sensors 100.

In the apparatus shown in FIG. 11A, signals generated in an amplification circuit are amplified, and 6 MHz ultrasonic waves from an ultrasonic probe are output through water in a container. Ultrasonic reflected waves reflected by a reflecting plate on the bottom of the container reach the ultrasonic probe, and the wave reception signals are amplified by the amplification circuit. The amplified wave reception signals are incorporated into a computer after passing through an A/D converter, and damping ratio is measured relative to a predetermined output level. First, damping ratio is measured without covering the ultrasonic probe, after which damping ratio is measured after fastening a polyimide film of a prescribed thickness to the ultrasonic probe so as to cover the surface. Here, polyimide films having thicknesses of 15 µm, 30 µm, 70 µm, 145 µm, 215 µm and 280 µm were used, and damping ratio was measured in each case.

According to the results shown in FIG. 11B, in contrast to damping ratio measured without covering the ultrasonic probe being about 0.1 dB, damping ratios in the case of covering with polyimide films of 15 µm and 30 µm were about 1 dB, damping ratio in the case of covering with a 70 µm polyimide film was about 1.5 dB, and damping ratio in the case of covering with a 145 µm polyimide film was about 1.1 to 1.9 dB. In addition, damping ratio in the case of covering the ultrasonic probe with a 215 µm polyimide film was about 3.5 to 4.0 dB, and that in the case of covering with a 280 µm polyimide film was about 8.0 to 8.5 dB.

During measurement of ultrasonic waves, damping of about 2 dB is considered to have hardly any effect in terms of visualizing resulting ultrasound images. Thus, since there are hardly any effects on ultrasonic wave measurement up to a thickness of 145 µm, and the thickness of piezoelectric sensors 100, including the piezoelectric layer and electrode layers, is roughly 20 µm or less, the piezoelectric sensors used in the ultrasound diagnostic apparatus 1 of the present invention can be said to be thin enough so as not to have an effect on ultrasonic wave signals.

In addition, since piezoelectric sensors 100 have superior heat resistance, they can be disinfected by boiling. Moreover, since they are composed of a flexible, film-like substrate, they are able to flexibly fit specimen surfaces and ultrasonic probe surface 10a even if these surfaces are curved, thereby improving measurement reliability.

Furthermore, the number of piezoelectric sensors 100 or the width or arranged location and so forth of each piezoelectric sensor are not limited to those shown in FIG. 2, but rather may be set as desired according to the particular application. In addition, piezoelectric sensors 100 may be made so as not to be exposed on the surface by, for example, covering all of the piezoelectric sensors 100 with a thin, vinyl sheet. Namely, the piezoelectric sensors may be arranged in the vicinity of the ultrasonic probe surface 10a.

[Other Examples of Piezoelectric Sensors 100]

Figure 12:
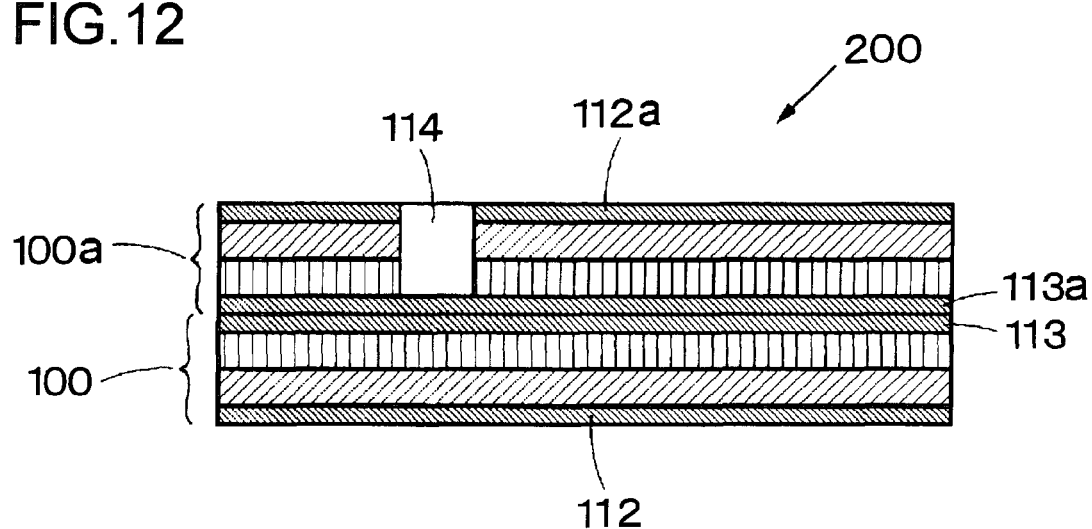
FIG. 12 is a cross-sectional view showing the configuration of another form of a piezoelectric sensor.

FIG. 12 is a cross-sectional view showing the configuration of another form of a piezoelectric sensor 200. This piezoelectric sensor 200 is composed by laminating two layers of the piezoelectric sensor 100 shown in FIG. 10. This piezoelectric sensor 200 is fabricated in the manner described below. First, as explained in FIG. 10, piezoelectric sensor 100 is fabricated by laminating piezoelectric layer 111, first electrode layer 112 and second electrode layer 113 on substrate 110. Connecting hole 114 for connecting a detection terminal, lead wire and the like to the electrode layers is formed in another piezoelectric sensor to obtain piezoelectric sensor 100a.

The piezoelectric sensors 100 and 100a are then superimposed and adhered so that the second electrode layer 113 side of piezoelectric sensor 100 contacts the second electrode layer 113a side of piezoelectric sensor 100a. Second electrode layer 113 and second electrode layer 113a are then electrically connected. A detection terminal, lead wire and the like are connected to second electrode layer 113a through the connecting hole 114. The first electrode layer 112 and first electrode layer 112a are also electrically connected. The other detection terminal, lead wire and the like are then connected to the first electrode layer 112 and first electrode layer 112a.

Since piezoelectric sensor 200 is composed by laminating two layers of piezoelectric sensors corresponding to piezoelectric sensor 100 in this manner, the surface area of the piezoelectric layer that receives pressure is doubled, thereby allowing the obtaining of a highly sensitive pressure sensor. Since piezoelectric sensor 200 employs a structure in which the interior thereof is shielded by first electrode layer 112 and first electrode layer 112a, S/N ratio can be improved by eliminating electromagnetic induction noise and the like from the outside. Furthermore, although second electrode layer 113 and second electrode layer 113a are laminated so as to be located on the outside, positioning second electrode layer 113 on the inside as shown in the drawing is preferable in terms of protecting piezoelectric layers 111 and 111a.

In addition, although two piezoelectric sensors 100 and 100a are superimposed and laminated in FIG. 12, a single piezoelectric sensor 100 may be laminated by folding over so that second electrode layer 113 is positioned on the inside. In this case as well, connecting hole 114 is formed in advance at a suitable location in piezoelectric sensor 100. Furthermore, although an adhesive such as silicon rubber or epoxy is used to adhere the piezoelectric sensors, silicon rubber is preferable for maintaining the flexibility of the sensor.

Figure 13:
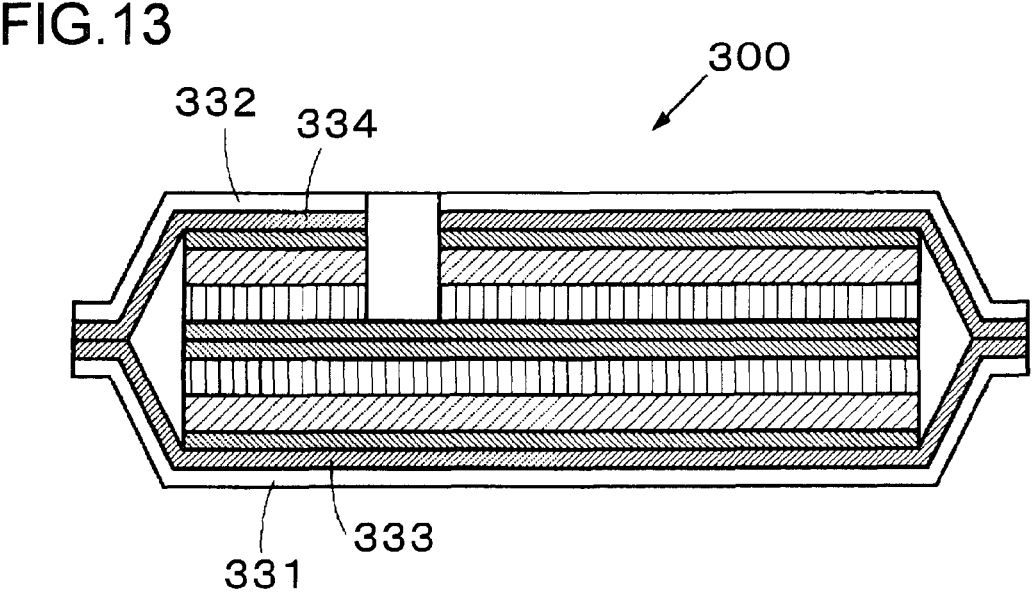
FIG. 13 is a cross-sectional view showing the configuration of still another form of a piezoelectric sensor.
Figure 19A:
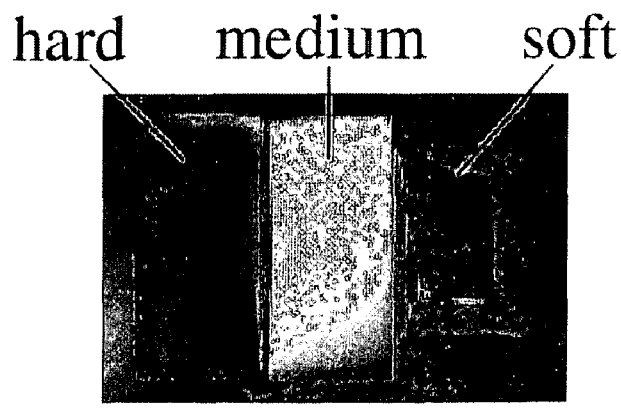
Figure 19B:
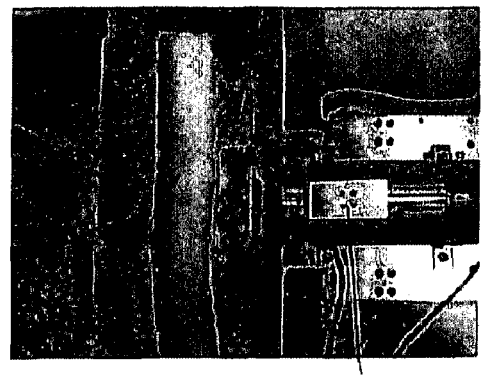
FIG. 19B depicts an ultrasonic probe in which piezoelectric sensors are arranged being pressed into the layered structure.

FIG. 13 is a cross-sectional view showing the configuration of still another form of a piezoelectric sensor 300. Although this piezoelectric sensor 300 corresponds to piezoelectric sensor 200 shown in FIG. 12, protective films 331 and 332 are adhered to both the upper and lower sides so as to cover the entire sensor. Heat resistance and durability are further improved as a result of the piezoelectric sensor body being protected by protective films 331 and 332. Forming metal shielding layers 333 and 334 on each protective films 331 and 332, respectively, improves shielding against electromagnetic induction noise and the like, thereby making it possible to further improve S/N ratio.

Furthermore, the thicknesses of piezoelectric sensors 200 and 300 shown in FIGS. 12 and 13 can be made to be about 60 μm overall. Consequently, the resulting piezoelectric sensors are in the form of an extremely thin film, and effects on ultrasonic wave signals can be reduced considerably. As was previously described, since piezoelectric sensors have hardly any effect on ultrasonic wave measurement up to a thickness of 145 μm, piezoelectric sensors 200 and 300 can be said to be thin enough so as not to have an effect on ultrasonic wave signals when used as piezoelectric sensors used in the ultrasound diagnostic apparatus 1 of the present invention. In addition, since these piezoelectric sensors 200 and 300 have superior heat resistance in the same manner as piezoelectric sensor 100, they can be disinfected by boiling, and since they are composed of a flexible, film-like substrate, they are able to flexibly fit specimen surfaces and ultrasonic probe surface 10a even if these surfaces are curved, thereby improving measurement reliability.

[Elasticity, Viscosity and Inertia Estimation Function]

As will be explained below, the ultrasound diagnostic apparatus 1 as claimed in the present invention is able to estimate the amount of fluctuation of each tissue layer that composes a specimen based on an equation of motion of a physical model, as well as estimate values of elasticity, viscosity and inertia for each of a plurality of tissue layers that compose a specimen based on output signals from piezoelectric sensors 100. The following provides an explanation of this function.

FIG. 17 shows an example of a physical model used to estimate elasticity, viscosity and inertia in the present invention. This drawing represents a specimen having a three-layer structure as shown in FIG. 17A with a physical model composed of elasticity, viscosity and inertia as shown in FIG. 17B. A multi-dimensional model can be generated in a similar manner. For example, a two-dimensional model can be generated as shown in FIG. 17C, and in the case of a three-dimensional model, a model can be generated by layering this two-dimensional model.

Here, x1, x2 and x3 indicate the locations of boundaries within the layers measured with ultrasonic probe 10, and the amount of movement at these locations, namely the amount of fluctuation of each tissue layer that composes the specimen, is measured in the manner described below by the previously described image processing unit 50.

FIG. 18 is a schematic drawing of a signal received by ultrasonic probe 10. Since this ultrasonic wave signal is strongly reflected at locations where viscoelasticity (acoustic impedance) changes within the specimen tissue, a change in amplitude that reflects this change appears in the signal. Here, when considering the case in which the shape of the specimen changes as a result of ultrasonic probe 10 being pressed against the specimen, the shape of the signal received at times t and t+1 can be determined to shift.

Furthermore, in the example of time shown in FIG. 18, the time interval between time t and time t+1 is 1 msec, and the maximum value of the horizontal axis of each graph is about 50 usec. However, this value can be adjusted as desired according to the movement velocity of ultrasonic probe 10, and for example, in the case of moving slowly, it is not necessary to use that large a time interval, while in the case of conversely moving rapidly, it is preferable to use a short time interval.

Therefore, by finely dividing the pattern of received signals on the time axis, the manner in which a certain zone at time t has moved in the direction in which the ultrasonic probe 10 has been pressed (one dimension) at time t+1 can be calculated by calculating the correlation value on the pattern at time t+1, thereby making it possible to determine the manner in which the specimen was deformed. At this time, soft areas are calculated to have large deformation, while hard areas are calculated to have little deformation. Moreover, by allowing processing to proceed consecutively in the manner of time t+1, t+2, t+3 and so on, the manner in which each site changes in response to pressing by ultrasonic probe 10 can be obtained in the form of a time series.

Processing can be carried out in the exact same manner even in cases in which two-dimensional image data or three-dimensional image data is able to be received as a result of ultrasonic probe 10 having multiple channels or as a result of scanning. In other words, where each zone moves (in two dimensions or three dimensions) can be measured by preparing target data at time t and time t+1, and dividing the data into detailed regions within the target space.

Returning to FIG. 17B, m1, m2 and m3 represent the mass within each region, k1, k2 and k3 represent the modulus of elasticity of each region, b1, b2 and b3 represent the coefficient of viscosity of each region, and f represents the force by which ultrasonic probe 10 acts on the specimen. At this time, an equation of motion of a physical model describing the elasticity, viscosity and inertia of the specimen as well as the relationship between the force applied to the specimen and the amount of deformation of the specimen is composed in the manner shown below.

$$m_1\ddot{x}_1 + b_1(\dot{x}-\dot{x}_2) + k_1(x_1-x_2) = f$$

$$m_2\ddot{x}_2 + b_2(\dot{x}_2-\dot{x}_3) + k_2(x_2-x_3) - b_1(\dot{x}_1-\dot{x}_2) - k_1(x_1-x_2) = 0$$

$$m_3\ddot{x}_3 + b_3\dot{x}_3 + k_3x_3 - b_2(\dot{x}_2-\dot{x}_3) - k_2(x_2-x_3) = 0 \quad \text{[Equation 1]}$$

In the above equation, x1, x2 and x3 can be calculated in the manner described above, and their first-order and second-order differentials can also be calculated. In addition, f is a measured value measured from the output signals of piezoelectric sensors 100. Unknown quantities in the above equation consist of the nine quantities of m1, m2, m3, b1, b2, b3, k1, k2 and k3. However, since known parameters vary with time and can be calculated at each time, a simultaneous equation for the measured time can be constructed. Thus, unknown parameters can also be calculated using numerical analyses. Thus, elasticity, viscosity and inertia can be estimated for each tissue layer that composes a specimen. Specific measurement examples will be subsequently described using FIGS. 19 to 25.

[Action of Ultrasound Diagnostic Apparatus 1]

Figure 3:
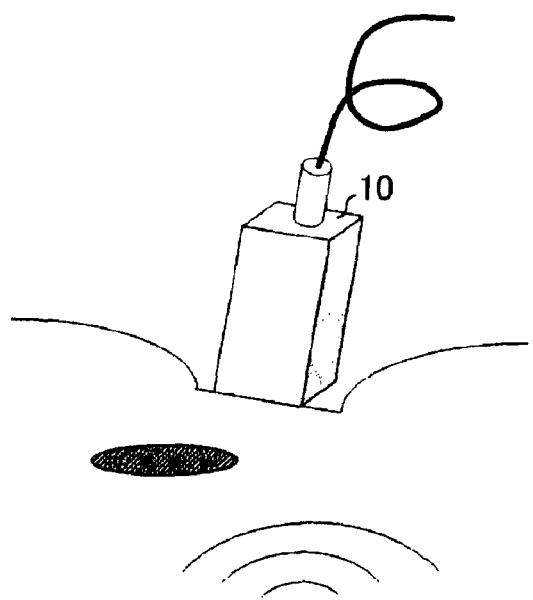
FIG. 3 is a schematic drawing of an ultrasonic probe, specimen and interior thereof during acquisition of an ultrasound tomographic image of a specimen.

The following provides an explanation of the action of ultrasound diagnostic apparatus 1 of the present invention using FIGS. 3 to 9. FIG. 3 is a schematic drawing of an ultrasonic probe 10, a specimen and the interior thereof during acquisition of an ultrasound tomographic image of a specimen using the ultrasonic probe 10. In nearly all cases, since the surface of the specimen is not uniform as shown in the drawing, there is no guarantee that the ultrasonic probe 10 will contact the specimen completely perpendicular to the specimen. In addition, since there are areas within the specimen that physically fluctuate over time (such as the heart, muscle, vascular arteries and the like in the case of humans), there are forces that propagate to the surface of the specimen accompanying those fluctuations.

Namely, since reaction force generated as a result of ultrasonic probe 10 contacting the specimen, and force generated spontaneously from the interior of the specimen interact in a complex manner, it is impossible for them to be uniform on surface 10a of ultrasonic probe 10. In this manner, the status of pressure distribution on ultrasonic probe surface 10a when generating an ultrasound tomographic image varies considerably, and measuring this status of pressure distribution makes it possible to determine under what type of pressure conditions the ultrasound tomographic image was obtained, thereby enabling acquisition of a larger amount of information relating to the specimen.

Figure 4A:
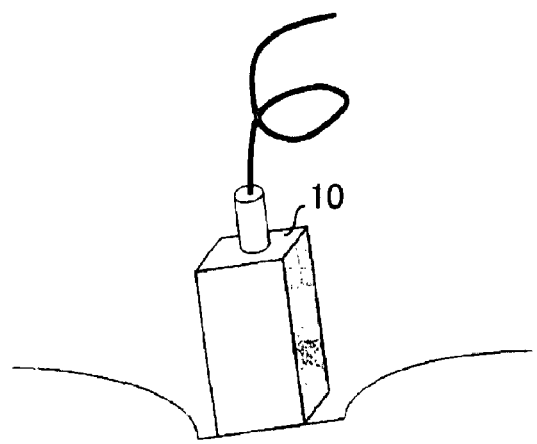
Figure 4B:
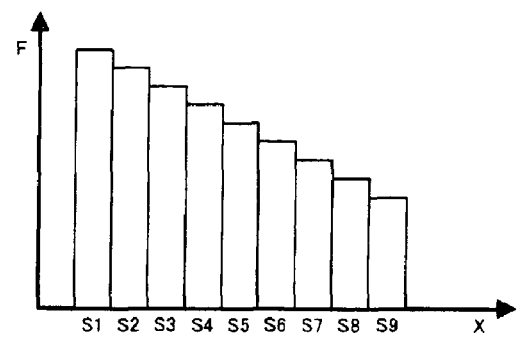
FIG. 4B shows an example of a histogram of pressure distribution measured at that time.

FIG. 4A is a schematic drawing depicting contact by ultrasonic probe 10 with a specimen while positioned at an angle, while FIG. 4B shows a histogram of pressure distribution measured at that time. In this example, piezoelectric sensors 100 are assumed to be arranged in the form of an array on ultrasonic probe surface 10a. Sensor output signal processing unit 40 outputs pressure measured for each piezoelectric sensor S1 to S9 based on output signals from each piezoelectric sensor 100 to image processing unit 50. In image processing unit 50, a histogram is generated for the pressure corresponding to each piezoelectric sensor S1 to S9, and that histogram along with the resulting ultrasound tomographic image, obtained by plotting piezoelectric sensors 100 on the X axis and the corresponding pressure on the Y axis, is output to monitor 60.

In this manner, since it is possible to measure pressure on ultrasonic probe surface 10a directly, values of higher reliability can be obtained as compared with methods that estimate pressure indirectly. In addition, it is possible to measure pressure distribution on ultrasonic probe surface 10a, and pressure distribution on ultrasonic probe surface 10a can be measured in detail by arranging piezoelectric sensors 100 in the form of an array. Moreover, since pressure distribution can be represented in the form of a histogram, the pressure distribution on ultrasonic probe surface 10a can be ascertained. More specifically, pressure can be determined to be decreasing in the order of S1 to S9 based on the pressure distribution shown in FIG. 4B, and an apparatus user is able to infer that ultrasonic probe 10 is contacting the specimen on an angle (in other words, the ultrasonic probe 10 is pressing stronger at S1 and contacting the specimen weakly at S9).

The absence of uniformity of pressure distribution means that stress distribution within the specimen is not uniform. In other words, the apparatus user observes a distorted ultrasound tomographic image. If pressure distribution is able to be determined by the present invention, the user is able to overcome this problem by adjusting the amount of pressure applied when pressing the specimen with the ultrasonic probe 10 (by pressing less at S1 and pressing stronger at S9).

Figure 5A:
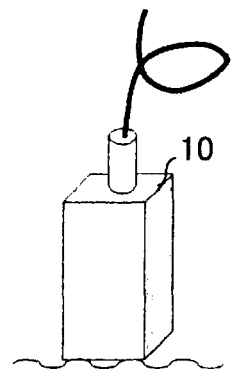
Figure 5B:
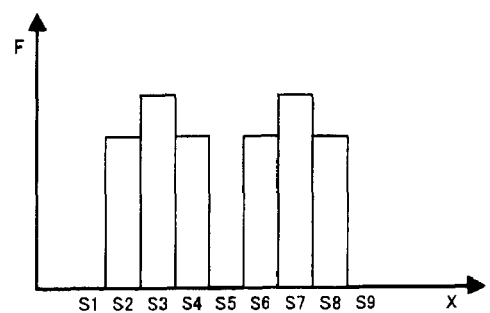
FIG. 5B shows an example of a histogram of pressure distribution measured at that time.

FIG. 5A is a schematic drawing depicting contact by ultrasonic probe 10 with a specimen having surface irregularities in the surface thereof, while FIG. 5B shows a histogram of pressure distribution measured at that time. In this example, there is unevenness in pressure distribution due to the surface irregularities, and this indicates unevenness in the surface texture or hardness distribution and so forth of the specimen.

In the histogram of FIG. 5B in particular, although there are regions where pressure is not detected as in the case of S1, S5 and S9, this indicates that piezoelectric sensors S1, S5 and S9 on ultrasonic probe surface 10a are positioned at concave portions of the specimen surface thereby preventing contact with the specimen. An apparatus user is thus able to ascertain a rough approximation of irregularities present in the surface of the specimen on the basis of this information.

Figure 6A:
Figure 6A:
Figure 6B:
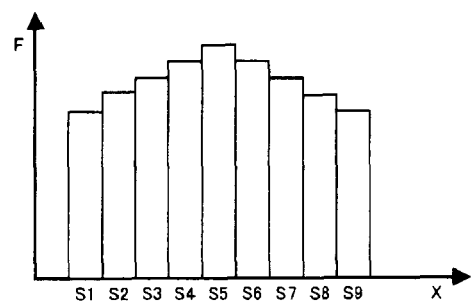
FIG. 6B shows an example of a histogram of pressure distribution measured at that time.

FIG. 6A is a schematic drawing depicting contact by an ultrasonic probe 10 with a specimen containing a hard area in the interior thereof (represented with a black shadow in the drawing), while FIG. 6B shows an example of a histogram of pressure distribution measured at that time. As in this example, in the case a hard area is contained within a specimen, the output signal of piezoelectric sensor S5 in contact with a proximal surface of that area is the largest, and output signals become smaller at locations moving away from that area.

At this time, although it is difficult to judge whether the cause of the resulting pressure distribution is caused by the shape of the surface of the specimen, the hardness distribution of the surface, or the presence of a hard foreign substance contained therein based on pressure distribution information alone, the cause of that distribution can be determined by comparing ultrasound tomographic images.

Figure 7A:
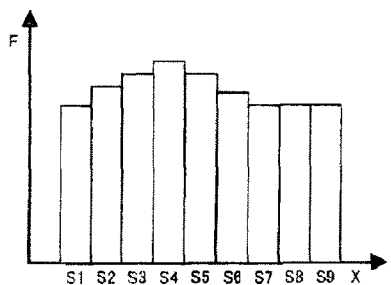
Figure 7A:
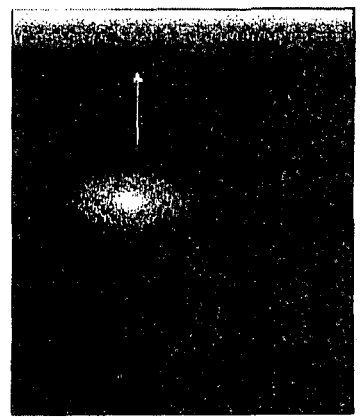
Figure 7B:
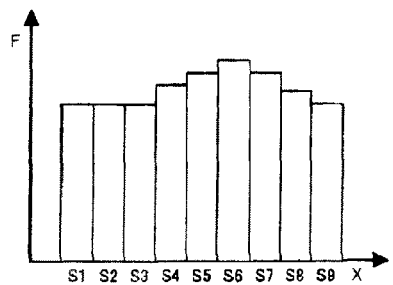
FIG. 7B shows a second example of the same display.
Figure 7B:
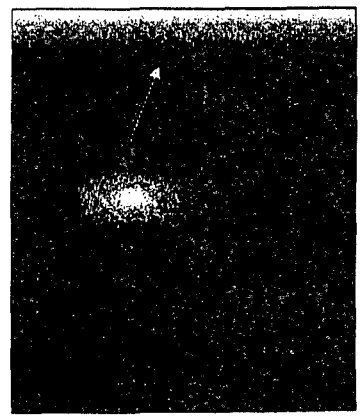
Figure 8:
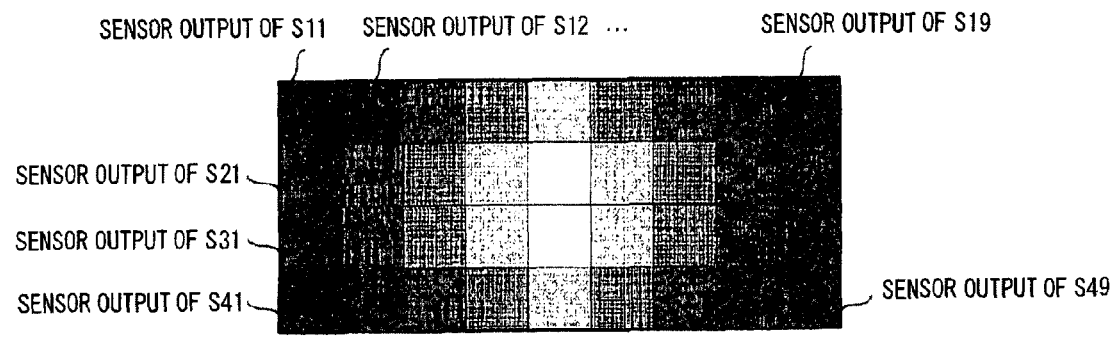
FIG. 8 is an example of a two-dimensional image of pressure distribution obtained in the case of piezoelectric sensors being arranged in the form of a matrix.

FIGS. 7A and 7B are examples of respectively displaying a histogram of pressure distribution and an ultrasound tomographic image on the top and bottom of monitor 60. In this example, an ultrasound tomographic image as shown in the lower half of FIG. 7 is displayed, and the oval white shadow, or area of high luminosity, indicates that the area has high hardness. Here, if piezoelectric sensors 100 are arranged on ultrasonic probe surface 10a in the form of an array at equal intervals at regions where ultrasonic oscillators are arranged, the histogram and image can be compared provided each piezoelectric sensor S1 to S9 is evenly arranged in a row in the form of an array on the X axis of the ultrasonic wave image shown in the lower half of the drawing. In this manner, since an ultrasound tomographic image is output so as to be able to be compared with pressure distribution, it is possible to determine under what type of pressure conditions the ultrasound tomographic image was obtained.

For example, when the pressure distribution obtained at this time is represented with a histogram like that shown in FIG. 7A, the output of S4 located directly above the area of high hardness is the largest, and since output decreases moving away from that area, pressure can be inferred t be acting in the direction of the arrow in the ultrasound tomographic image shown in the lower half of FIG. 7A, namely in the direction extending directly upward from the area of high hardness. On the other hand, when the pressure distribution obtained at this time is represented with a histogram like that shown in FIG. 7B, the output of S6 located on an angle upward and to the right from the area of high hardness is the largest, and since output decreases moving away from that area, pressure can be inferred to be acting in the direction of the arrow in the ultrasound tomographic image shown in the lower half of FIG. 7B, namely in the direction extending upward at an angle to the right from the area of high hardness.

Furthermore, in cases in which the locations of the peaks of the histogram are located at locations well away from an area of high hardness, and in cases in which an area of high hardness is not present, the generation of the peaks can be presumed to be caused by the condition of the specimen surface or manner in which contact is made by the ultrasonic probe. In this manner, since an ultrasonic tomographic image can be compared with pressure distribution, it is possible to determine under what type of pressure conditions the ultrasound tomographic image was obtained.

FIG. 8 is an example of a two-dimensional image of pressure distribution obtained in the case of piezoelectric sensors 100 being arranged in the form of a matrix on ultrasonic probe surface 10a as shown in FIG. 2B. Here, piezoelectric sensors S11 to S49 are arranged on ultrasonic probe surface 10a in the form of a matrix at equal intervals at regions where ultrasonic oscillators are arranged, and image processing unit 50 determines the luminosity of pixel blocks corresponding to each piezoelectric sensor so as to be proportional to the output signal level of the piezoelectric sensors, and generates a two-dimensional image that is output to monitor 60. In this example of FIG. 8, the luminosities of S25 and S35 located in center are the highest, indicating that the pressure applied to those piezoelectric sensors 100 is the highest. Since luminosity decreases moving away from these sensors, pressure can be determined to decrease the farther away from the center. Since the luminosities of sensors S11, S19, S41 and S49 located in the four corners are the lowest, the pressure applied to these piezoelectric sensors 100 can be determined to be the lowest.

In this manner, as a result of the piezoelectric sensors being arranged in the form of a matrix, pressure distribution on the ultrasonic probe surface can be measured in detail, and since the measured pressure distribution can be displayed in the form of a two-dimensional image, a detailed pressure distribution on ultrasonic probe surface 10a can be ascertained at a glance.

Figure 9A:
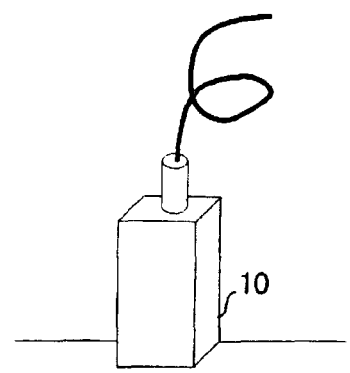
FIG. 9A is a schematic drawing depicting measurement of force propagating from a fluctuation site.
Figure 9B:
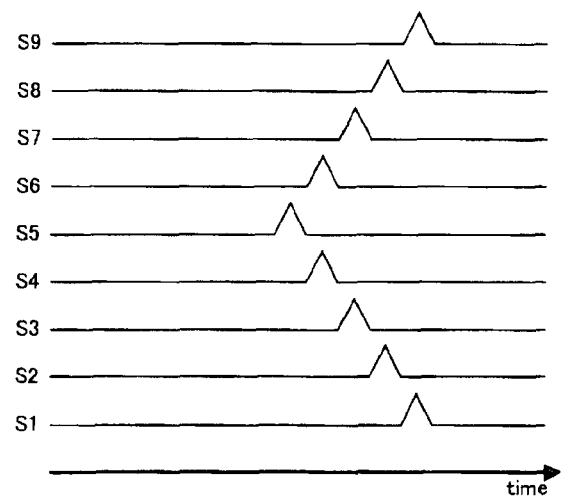
FIG. 9B shows a first example of expressing time series data of output signals measured at that time.
Figure 9C:
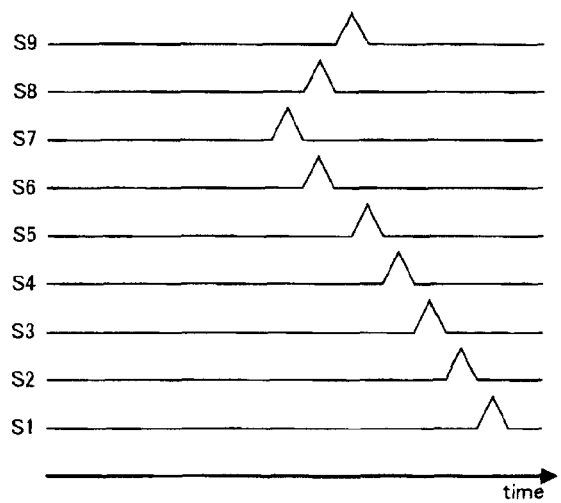
FIG. 9C is a second example of the same data.

FIG. 9A is a schematic drawing depicting measurement of force being generated from within a specimen, namely force propagating from a fluctuation site, while FIG. 9B and FIG. 9C show time series data of output signals measured at that time. As was previously described, sensor output signal processing unit 40 stores output signals from each piezoelectric sensor 100 for a prescribed amount of time in the form of time series data, and is able to carry out the processing described below based on that time series data.

For example, a time waveform of output signals as shown in FIG. 9B are assumed to be obtained from each piezoelectric sensor S1 to S9 arranged in the form of an array. In this waveform data, time (amount of time elapsed from a prescribed time) is plotted on the horizontal axis. Here, an area within a specimen is assumed to fluctuate and a single-event signal, namely pressure, is assumed to be generated and propagate to the specimen surface. Signals output from piezoelectric sensors 100 at this time are represented by prescribed signals in the form of triangle waves.

In the example shown in FIG. 9B, the output time of the signal from piezoelectric sensor S5 is the shortest, and signal times gradually become longer moving away from the piezoelectric sensor. In this manner, time differences can be seen to exist between the pressure arrival times. Sensor output signal processing unit 40 specifies the piezoelectric sensor that outputted this prescribed signal the fastest, outputs that piezoelectric sensor to image processing unit 50, and image processing unit 50 outputs a piezoelectric sensor number (for example, the fifth sensor in the case of sensor S5) for specifying this piezoelectric sensor to monitor 60. As a result, the fluctuating area serving as the signal source can be located closest to S5, namely below S5.

In addition, in the example shown in FIG. 9C, the output time of the signal from piezoelectric sensor S7 is the shortest, and output times gradually become longer the farther from that piezoelectric sensor. As a result, the fluctuating area serving as the signal source can be inferred to be located closest to S7, namely below S7. In this manner, the piezoelectric sensor 100 at the shortest distance from a fluctuating area within a specimen can be specified, and the location of that fluctuating area within the specimen can be specified from the location of that piezoelectric sensor on the ultrasonic probe surface.

In addition, the time difference between output times of the output signals in the form of triangle waves can be calculated from the time series data, while the velocity of signals propagating in response to a fluctuation within the specimen (provided the velocity is in the direction of the X axis) can be calculated from the interval between piezoelectric sensors 100. For example, if the time difference between output times of S5 and S6 is 10 msec, and the interval between S5 and S6 is 1 cm, the velocity of the signal propagated from a fluctuating area is 0.01 m/10 msec=1 m/sec. In addition, if the output interval of triangular waves with respect to S5 is 10 seconds, for example, then the signal propagating from the fluctuating area is specified to be appearing at a period of 10 seconds.

Next, the results of carrying out calculations around the periphery of the carotid artery using ultrasound diagnostic apparatus 1 of the present invention are shown in FIGS. 14 to 16. In an ultrasound diagnostic apparatus used in this example, as shown in FIG. 14, eight piezoelectric sensors 100 consisting of S1 to are arranged in the form of an array on surface 10a of ultrasonic probe 10. As shown in FIG. 15, ultrasonic wave measurement and pressure measurement are carried out by placing surface 10a in contact with the skin in the vicinity of the carotid artery. As a result, an ultrasound tomographic image as shown in FIG. 16A and times series pressure data measured with each piezoelectric sensor 100 shown in FIG. 16B are obtained.

A signal of maximum amplitude can be ascertained to be output from piezoelectric sensor 100 designated as S5 based on the time series data of each channel shown in FIG. 16B, and amplitude can be seen to gradually decrease moving away from S5. As shown in FIG. 16B, an ultrasound tomographic image is displayed on monitor 60 next to the time series data. At this time, in addition to the numbers of the piezoelectric sensors 100 corresponding to each image region being displayed to the right of the corresponding image region, the output signals of the corresponding piezoelectric sensors 100 are also displayed to the right of the corresponding image regions. Thus, the output signal corresponding to each image region can be ascertained at a glance, thereby demonstrating the extraordinary effect of being able to determine the manner in which pressure has fluctuated in each ultrasound tomographic image region.

Moreover, as shown in FIG. 16B, as a result of emphasizing the display of the number of the channel (S5) that has output the signal having the maximum amplitude by displaying inside a box, that channel can be inferred to be closest to the fluctuation site, while the image region corresponding to that channel and the fluctuation site within the image region (here, the carotid artery) can be easily specified from the ultrasound tomographic image of FIG. 16A. Maximum amplitude referred to here is the amplitude for which the mean value obtained from ten measurements of peak-to-peak amplitude over a span of 1 second reaches a maximum. Furthermore, a fluctuation site can be evaluated extremely easily by providing an assist function that facilitates identification of the image region and fluctuation site by, for example, providing an enlarged display of the image region corresponding to the specified channel (FIG. 16A).

Here, the advantage of estimating the location of a fluctuation site based on peak-to-peak amplitude is that the estimation is not affected by the manner in which ultrasonic probe 10 is contacted with the specimen or any local changes in pressure. Namely, even if any unevenness occurs in pressure within a contact surface due to the manner in which the ultrasonic probe 10 contacts the specimen or local changes in pressure, since the time-based change in pressure that occurs is gradual, the peak-to-peak amplitude attributable thereto is an extremely low value as compared with the amplitude attributable to a fluctuation site.

Elasticity, Viscosity and Inertia Estimation Example

The following provides an explanation of an example of estimating values for elasticity, viscosity and inertia for each of a plurality of tissue layers composing a specimen using FIGS. 19 to 25. FIG. 19A shows a layered structure composed of three tissue layers. As shown in the photograph, this layered structure is composed of three types of polymer gels having different levels of elasticity (soft, medium and hard). An ultrasonic probe 10 on which piezoelectric sensors 100 are arranged is used to press against the layered structure of a specimen followed by measurement of data at that time as shown in FIG. 19B.

Figure 20:
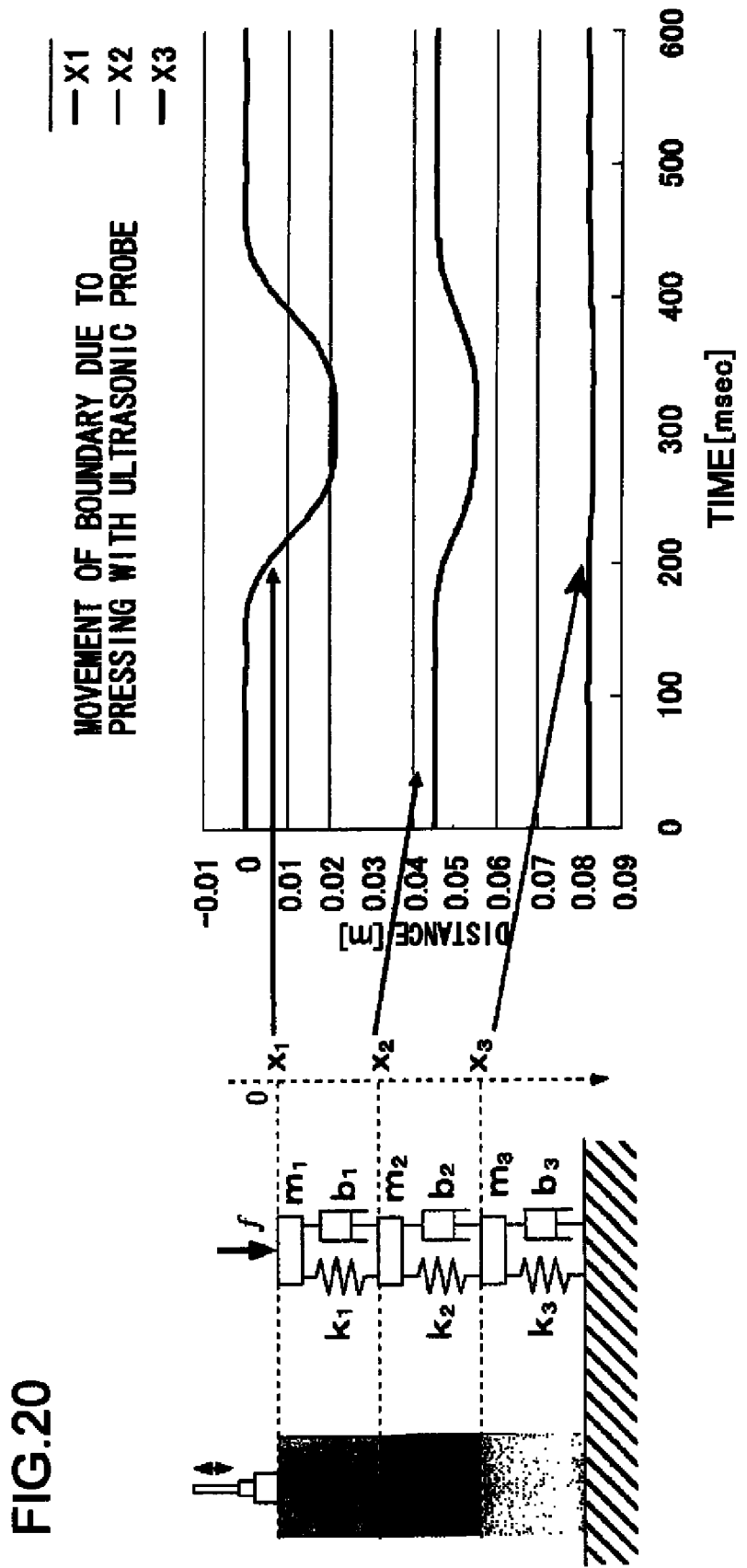
FIG. 20 is a graph showing the movement of the boundaries of a layered structure caused by pressing.

FIG. 20 is a graph showing the movement of the boundaries of a layered structure caused by pressing. Here, x1, x2 and x3 can be measured from ultrasonic wave signals and acquired in the form of time series data as previously described. As a result, the displacements and amounts of movement of x1, x2 and x3 resulting as a result of pressing with the ultrasonic probe 10 can be acquired in the form of time series data as shown in the graph. A relationship in the form of x1>x2>x3 can be determined from this graph to exist with respect to amount of movement. As a result, changes in the boundaries of this layered structure attributable to pressing can be ascertained.

Figures 21, 22:
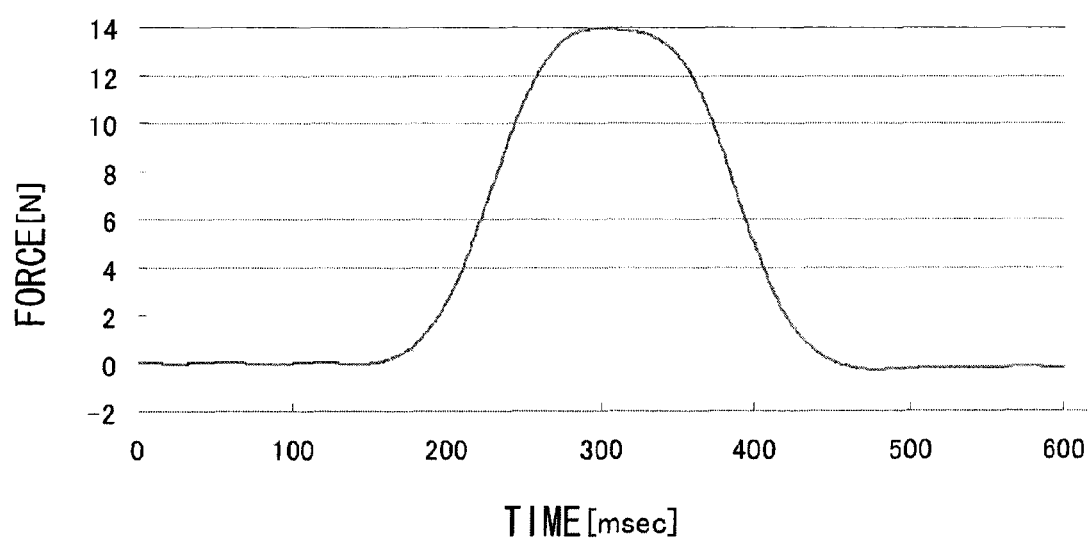
FIG. 21 is a graph showing changes in pressure during pressing.
FIG. 22 shows estimates for elasticity, viscosity and inertia for a tissue layer composed of a layered structure.

In addition, since output signals from piezoelectric sensors 100 can actually be measured, changes in pressure can be acquired in the form of time series data as shown in FIG. 21. Namely, since pressure changes and changes in boundaries can be acquired simultaneously, f, x1, x2 and x3 in the equation of motion of the above-mentioned physical model can be measured. In addition, by sampling a large number of parameters during the entire period pressure is being applied, the relationship among those parameters can be coalesced, thereby making it possible to estimate elasticity k, viscosity b and inertia m by numerical analyses.

As a result, as shown in the table of FIG. 22, elasticity, viscosity and inertia can be estimated for tissue layers 1, 2 and 3 of each polymer gel that composes a layered structure. An example of measurement using this estimation method is shown in FIGS. 23 to 25.

Figure 23:
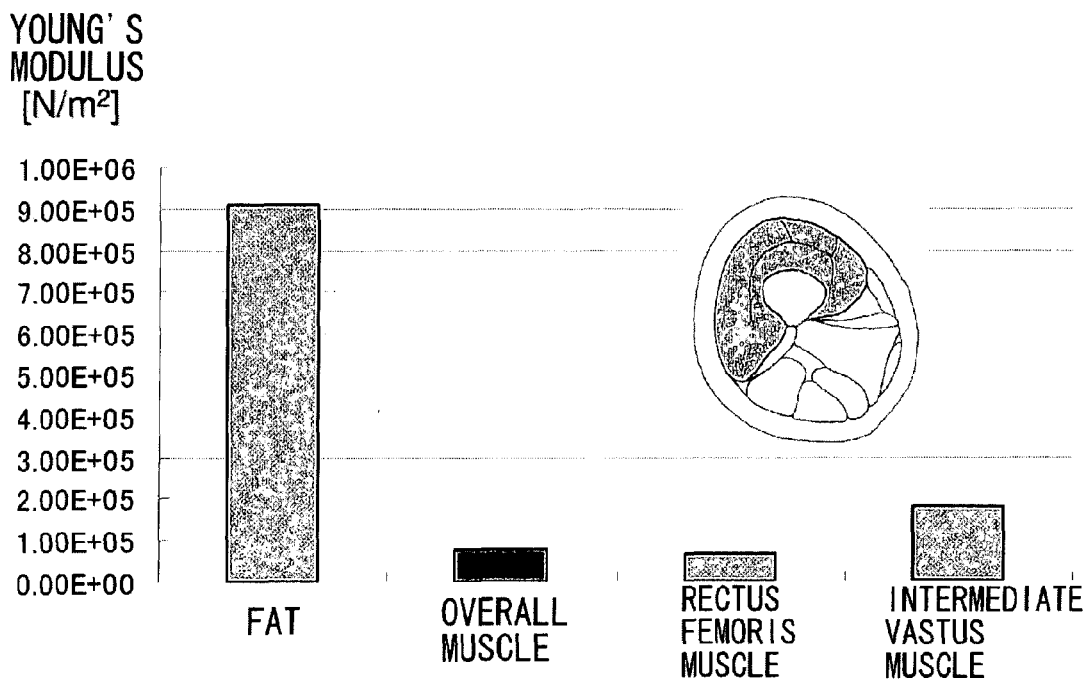
FIG. 23 shows the results of estimating elasticity for the thigh.

FIG. 23 shows the results of estimating elasticity for the thigh. Measurement was carried out using an ultrasonic probe 10 having 8 channels of piezoelectric sensors 100 as shown in FIG. 14. The results were obtained by applying an estimation method using the equation of motion of the physical model described above, estimating elasticity for each of the fat, intermediate vastus muscle and rectus femoris muscle tissue layers composing the thigh, calculating their respective resistance to elongation per unit surface area, namely Young's modulus, calculating Young's modulus for the entire muscle from these calculated values, and then graphing each calculated value. Young's modulus for each tissue layer can then be determined from these results.

Figure 24:
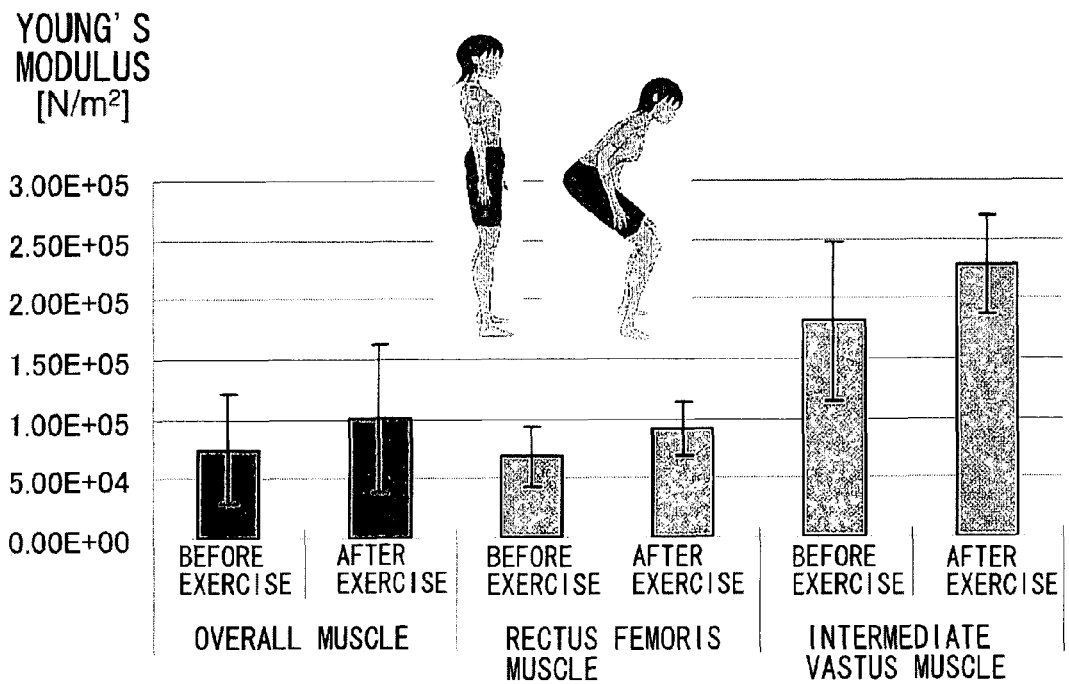
FIG. 24 shows the results of making estimates for the thigh before and after exercise; and, FIG. 25 shows the results of estimating elasticity of subcutaneous tissue and muscle in lymphedema patients and healthy subjects.

FIG. 24 shows the results of making estimates for the thigh before and after exercise. These results were obtained by estimating elasticity of each tissue layer of the intermediate vastus muscle and rectus femoris muscle before and after exercise, estimating overall muscle elasticity from these estimates, calculating Young's modulus for each and then graphing each calculated value. Young's modulus can be determined to be improved by exercise for both the intermediate vastus muscle and rectus femoris muscle based on these results. In addition, the effects of stretching exercises can be measured quantitatively by testing in this manner.

Figure 25:
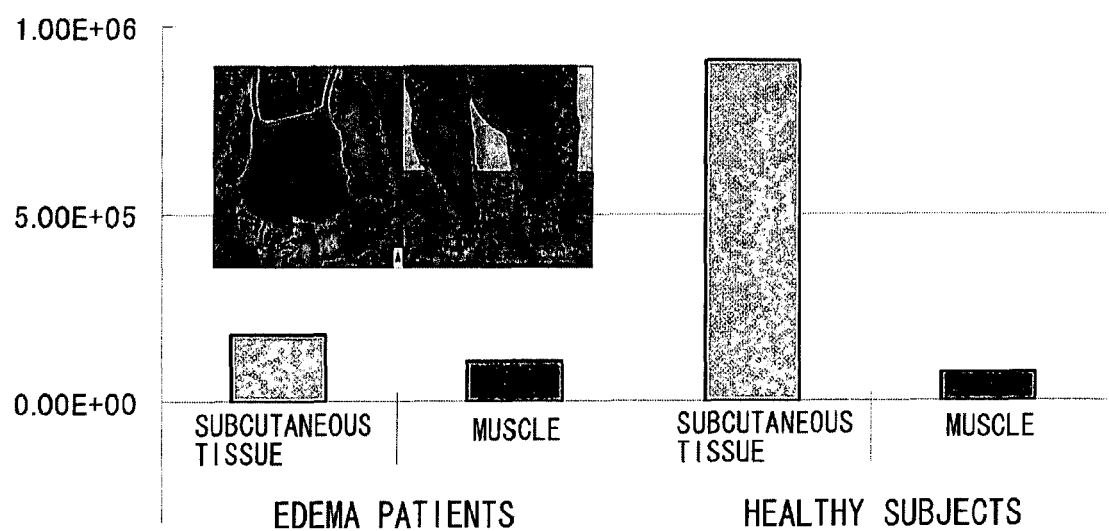

FIG. 25 shows the results of estimating elasticity of subcutaneous tissue and muscle in lymphedema patients and healthy subjects, calculating Young's modulus for each, and then graphing each calculated value. On the basis of these results, Young's modulus of subcutaneous tissue in lymphedema patients can be determined to be extremely low as compared with that of healthy subjects. Since this type of test can be performed, Young's modulus of subcutaneous tissue can be effectively used as an indicator for diagnosing lymphedema.

As has been indicated above, in the ultrasound diagnostic apparatus of the present invention, information such as the contact status of ultrasonic probe 10 with a specimen (including surface shape, hardness distribution and contact angle), reaction force generated by a specimen in response to ultrasonic probe 10 when pressed against the specimen, and force and vibrations generated within the specimen, can be measured in the form of the distribution of pressure acting on ultrasonic probe surface 10a.

The pressure distribution measurement function of ultrasound diagnostic apparatus 1 of the present invention is equivalent to providing an ultrasonic probe with a sense of touch in the manner of the palm of a human hand. As a result, a user holding the ultrasonic probe 10 is able to acquire information in the same manner as that acquired during palpation by a physician by changing the force applied during pressing and the direction in which it is applied. In addition, an ultrasound tomographic image (such as a B mode image) makes it possible to simultaneously ascertain the internal structure of a specimen as well as any deformations in that structure. Since all of these signals change with time, their behavior can be accumulated in the form of time series signals.

Thus, static information can be acquired by discontinuing movement of ultrasonic probe 10, while information including dynamics can be acquired by actively moving the ultrasonic probe 10. Combining this information makes it possible to acquire sophisticated information unable to be obtained with conventional ultrasonic probes.

Moreover, the ultrasound diagnostic apparatus 1 of the present invention is able to simultaneously acquire pressure changes and changes in boundaries. Consequently, in the case a specimen is composed of a plurality of tissue layers, the elasticity, viscosity and inertia of each tissue layer can be estimated based on an equation of motion of a physical model. As a result, measurement information previously unable to be obtained from ultrasonic tomographic images only or from pressure only can be used as indicators for analyzing a specimen. In particular, pressure distribution within a contact surface can be obtained in the form of measurement information by arranging a plurality of piezoelectric sensors 100 on surface 10a of ultrasonic probe 10, thereby making it possible to makes estimates of the contact surface in greater detail. Moreover, the use of sheet-like piezoelectric sensors enables highly accurate estimates without having an effect on ultrasonic wave information.

INDUSTRIAL APPLICABILITY

The ultrasound diagnostic apparatus of the present invention is able to provide new measurement information for use in the field of health care, the primary field in which ultrasonic probes are used. In addition, the ultrasound diagnostic apparatus of the present invention is able to provide new measurement information in the production and management processes of soft tissues (including silicon, rubber and other polymer materials). Moreover, the ultrasound diagnostic apparatus of the present invention is able to provide new measurement information food (including meats and vegetables) production and management processes.

The invention claimed is:

1. An ultrasound diagnostic apparatus provided with an ultrasonic probe which is configured to contact a specimen, and which generates an ultrasound tomographic image by transmitting and receiving ultrasonic waves through the ultrasonic probe, wherein
   a plurality of piezoelectric sensors, configured by using a film having a thickness of 145 µm or less as a substrate, arranged on or in the vicinity of a surface of the ultrasonic probe and in a region directly provided for transmission and reception of the ultrasonic waves,
   a measurer for measuring pressure distribution on or in the vicinity of the surface based on the arranged positions of each of the plurality of piezoelectric sensors on or in the vicinity of the surface thereof and output signals from the piezoelectric sensors, and a display for displaying the pressure distribution in a visible form; and
   the measurer accumulates an output signal in the form of time series data for each piezoelectric sensor for a prescribed amount of time, and measures a fluctuation status in the specimen or specifies the location of a fluctuation site based on time-based changes in the accumulated output signals and the arrangement of the piezoelectric sensors on or in the vicinity of the surface, wherein the piezoelectric sensors have a piezoelectric aluminum nitride thin film formed on the substrate.

2. The ultrasound diagnostic apparatus according to claim 1, wherein the display enables comparison between the accumulated output signals and the ultrasound tomographic image, and displays an output signal of each piezoelectric sensor while arranging in parallel image regions corresponding to the arrangement of the piezoelectric sensors in the ultrasound tomographic image.

3. The ultrasound diagnostic apparatus according to claim 1, wherein the measurer measures the velocity of prescribed signals between the plurality of piezoelectric sensors based on an arrangement interval of the piezoelectric sensors and an output time difference of the prescribed signals.

4. The ultrasound diagnostic apparatus according to claim 1, wherein the measurer measures the period of a prescribed signal of a specific piezoelectric sensor based on an output interval of the prescribed signal in the specified piezoelectric sensor.

5. The ultrasound diagnostic apparatus according to claim 1, wherein the measurer specifies the piezoelectric sensor that initially outputs a prescribed signal, and the display displays the arrangement of that piezoelectric sensor.

6. The ultrasound diagnostic apparatus according to claim 1, wherein the measurer specifies the piezoelectric sensor that outputs a signal for which the peak-to-peak amplitude reaches a maximum, and the display displays the arrangement of that piezoelectric sensor.

7. The ultrasound diagnostic apparatus according to claim 5 or claim 6, wherein the display displays the ultrasound tomographic image in a form that allows specification of an image region corresponding to the arrangement of the specified piezoelectric sensor.

8. The ultrasound diagnostic apparatus according to claim 7, wherein the display displays an enlarged view of the corresponding image region.

9. The ultrasound diagnostic apparatus according to claim 1, comprising a deformation amount measurer for measuring the amount of deformation of each tissue layer constituting the specimen, based on ultrasonic wave information obtained by the transmission and reception of ultrasonic waves, and
   an estimator for estimating the value of elasticity, viscosity or inertia of each of the tissue layers from a signal output of the piezoelectric sensors and the measured deformation amount of the specimen based on the elasticity, viscosity and inertia of the specimen along with an equation of motion of a physical model describing the relationship between force applied to the specimen and the amount of deformation of each layer constituting the specimen.

* * * * *